US00PP12448P2

(12) United States Plant Patent
Hanes

(10) Patent No.: US PP12,448 P2
(45) Date of Patent: Mar. 12, 2002

(54) GERANIUM PLANT NAMED 'FREE CHERRY ROSE'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 0 days.

(21) Appl. No.: 09/643,674

(22) Filed: Aug. 24, 2000

(51) Int. Cl.[7] ..... A01H 5/00
(52) U.S. Cl. ..... Plt./332
(58) Field of Search ..... Plt./332, 324

(56) References Cited

PUBLICATIONS

UPOV–ROM GTITM Computer Database 2001/02, Apr. 2, 2001, GTI Jouve Retrieval Software, Citation for Geranium 'Free Cherry Rose'.*

* cited by examiner

*Primary Examiner*—Bruce R. Campell
*Assistant Examiner*—June Hwu
(74) *Attorney, Agent, or Firm*—Rothwell, Figg, Ernst & Manbeck

(57) ABSTRACT

A new and distinct cultivar of ivy geranium plant named 'Free Cherry Rose', that is characterized by: green foliage, magenta flower color, and double flowers on large umbels, fast rooting and exhibits vigorous growth.

1 Drawing Sheet

BACKGROUND OF THE NEW PLANT

The present invention comprises a new and distinct cultivar of geranium, botanically known as *Pelargonium peltatum* Bailey, and hereinafter referred to by the cultivar name 'Free Cherry Rose'. The new cultivar is propagated from a seedling resulting from the cross of a seed parent 6342-2 and the pollen parent 5900-1, both unpatented.

'Free Cherry Rose' is a product of a planned breeding program intended to create new geranium cultivars with magenta colored flowers, double flower form, and superior cutting productivity.

The new cultivar was created in 1996 in Gilroy, Calif. and has been repeatedly asexually reproduced by cuttings in Gilroy, Calif. and Guatemala over a four year period. It has also been trialed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVAR

Figure 1:
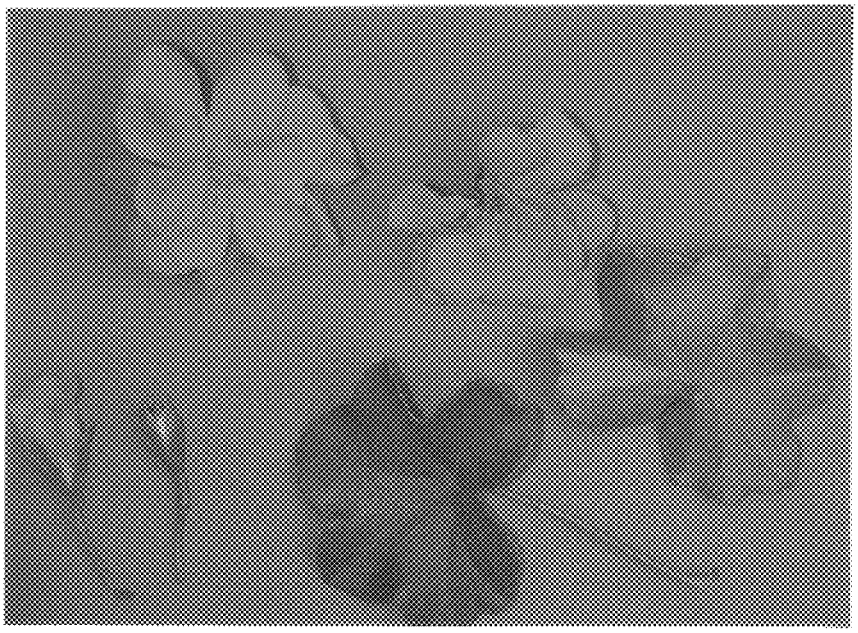
FIG. 1 is a close-up view of buds, blooms and leaves illustrating the color.
Figure 2:
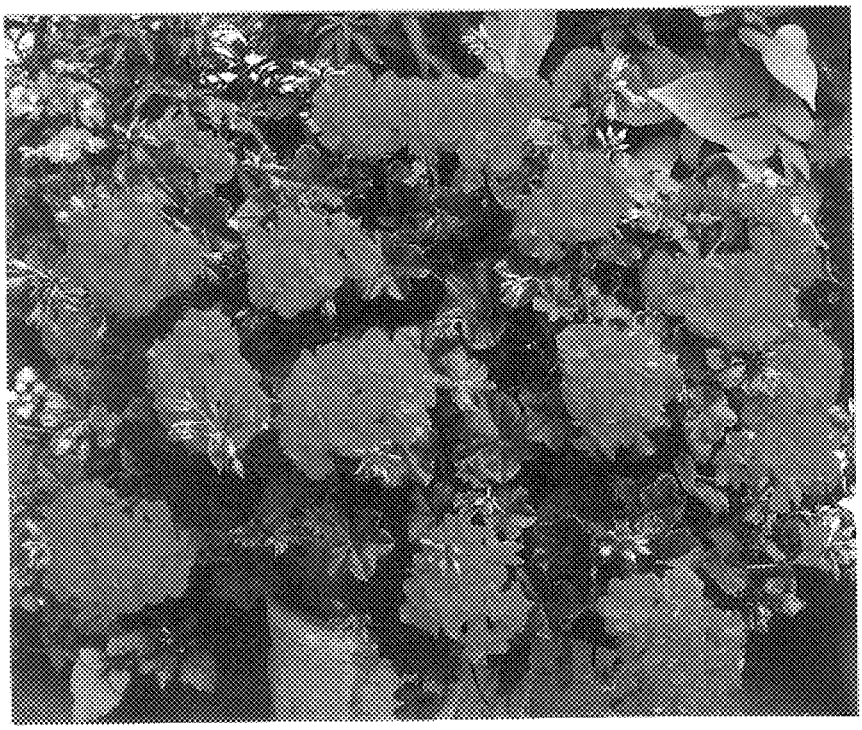
FIG. 2 is a view of the entire plant showing its form in pot culture when in full bloom.

The following detailed descriptions set forth the distinctive characteristics of 'Free Cherry Rose'. The data for these characteristics were collected from asexual reproductions carried out in Gilroy, Calif. The plant history was taken on 20 week old plants, blossomed under natural light in a greenhouse and color readings were taken in the greenhouse in Gilroy, Calif. on Jul. 10, 2000 under ambient light. Color references are primarily to The R.H.S. Colour Chart of The Royal Horticultural Society of London (R.H.S.).

The Plant

Classification:
- *Botanical.*—*Pelargonium peltatum.*
- *Commercial.*—Ivy geranium.

Form: Upright spreading, free branching.

Size: Height is 16 to 18 cm., as a 10 inch pot plant, excluding blooms; width is 28–36 cm.

Growth: Strong growth, good cutting producer and easy to root.

Foliage: Abundant quantity.

Leaves:
- *Size.*—Diameter about 6–7 cm.
- *Shape.*—Ivy shaped, nearly orbicular, with edges raised above the plane of the center of the leaf. Shallowly 5-angled lobed.
- *Margin.*—Entire, but ciliate.
- *Texture.*—Glabrous or almost glabrous on both upper and lower surfaces, except for pubescence along veins on lower surface.
- *Ribs and veins.*—Distinctly palmate, 3 to 4 cm. long. Veins on lower surface are Yellow-Green 146C–D RHS.
- *Color upper side.*—Yellow-green 146A RHS, with no zone.
- *Color under side.*—Slightly lighter green color, 146B RHS.
- *Petioles.*—About 3.5 to 6.5 cm in length.

The Bud

Size:
- *Diameter.*—About 8 mm.
- *Length.*—About 1.5 cm. at time of bud opening.

Shape: Pointed ovoid, or spindle shaped.

Color: Petals when sepals first divide, Red-purple 57A–B RHS.

Sepals: 5 in number, bent downwards behind petals. Pointed linear lanceolate, yellow-green 146C RHS in an open flower; 1.5 cm in length; 3 mm in width; base is truncate; apex is acuminate; texture is moderately pubescent.

The Flower

Blooming habit: Continuous throughout the year.

Size Approximately 5.5 cm. diameter, 1.5–2.0 cm. deep, irregularly radially symmetrical.

Form: Full double flower.

Petals: Approximately 20–23 petals 1.5–1.7 cm. wide and approximately 2.8–3.2 cm. long; shape is obovate/spatulate. Some of these petals are smaller inner petaloids of varying shape. Both the outer petals and inner petaloids are red-purple 57A RHS. Veins darker, red-purple 61B RHS, than interveinal regions, only on the upper surface of top two petals. Veins on the undersides of the other petals are usually white at the base. Color changing little with age. Petals and petaloids surface texture is soft and satiny.

Pedicel: Approximately 2.7–3.0 cm. in length; green 144A RHS.

Persistence: An open flower will hold its petals until the flower begins to dehisce, or approximately 7–10 days.

Inflorescence

Type: A 9–10 cm umbel composed of approximately 6–7 flowers, erect or laterally ascending.

Peduncle: Approximately 11–15 cm. in length, yellow-green 146B RHS in color; texture is scarcely pubescent, slightly scabrous.

Reproductive Organs

Stamens:

*Anthers.*—About 3–5 anthers positioned slightly above the mature stigma, red-purple 59A RHS prior to anthesis; approximately 2 mm in length.

*Filaments.*—White near base and mid length, graduating to red purple 57C RHS near anther; approximately 7 mm in length.

*Pollen.*—Orange 31A RHS in color.

Pistil:

*Number.*—1.

*Length.*—Approximately 11 mm.

*Stigma.*—5 linear lobes of near equal length, curling back toward ovary, purple-red 57C RHS.

Style:

*Length.*—About 2 mm.

*Color.*—Light green.

*Ovaries.*—At anthesis, densely pubescent with white hairs, oblong. Green drying to a light brown at maturity.

*Fruit.*—Occasional seed set; seed is approximately 3.8–4.0 mm in length; 1 mm in width; color is brown 177A RHS but may darken with age.

Fragrance: None.

Disease/insect resistance: No observed disease or insect susceptibility or resistance.

Comparison with parental cultivars: Parental cultivar 6342-2 has red colored, single flowers as compared to the magenta colored double flower of the present invention. Parental cultivar 5971-1 is also a red colored single flowered plant.

I claim:

1. A new and distinct cultivar of ivy geranium plant as shown herein named 'Free Cherry Rose' that is characterized by: green foliage, magenta flower color, and double flowers on large umbels, fast rooting and exhibits vigorous growth.

* * * * *